United States Patent [19]

Smith

[11] Patent Number: 5,176,129

[45] Date of Patent: Jan. 5, 1993

[54] SELF-RETAINING REFRACTOR

[75] Inventor: Stephen H. Smith, Riegelsville, Pa.

[73] Assignee: Tekdyne, Inc., Quakertown, Pa.

[21] Appl. No.: 663,382

[22] Filed: Mar. 1, 1991

[51] Int. Cl.⁵ .............................................. A61B 17/02
[52] U.S. Cl. ...................................... 128/20; 606/198
[58] Field of Search .................. 128/20; 606/119, 198

[56] References Cited

U.S. PATENT DOCUMENTS

| | | | |
|---|---|---|---|
| 1,170,324 | 2/1916 | Pomerene | 606/119 |
| 1,328,624 | 1/1920 | Graham | 606/198 |
| 2,234,715 | 9/1939 | Whitney | 606/198 |
| 2,651,300 | 11/1951 | Fehrman | 57/74 |
| 2,702,540 | 2/1955 | Debeh | 128/20 |
| 3,916,907 | 6/1974 | Peterson | 606/90 |
| 4,034,746 | 8/1975 | Williams | 128/20 |
| 4,502,485 | 3/1985 | Burgin | 128/20 |
| 4,854,300 | 8/1989 | Corbo | 128/20 |
| 5,030,224 | 7/1991 | Wright et al. | 128/20 |

FOREIGN PATENT DOCUMENTS 269293 11/1929 Italy ..................................... 128/20

OTHER PUBLICATIONS

Accurate Surgical & Scientific Instruments Corporation 1991 Catalog (G-1 Edition), cover page and pages 22, 26 & 27.

Primary Examiner—John J. Wilson

[57] ABSTRACT

A disposable self-retaining skin retractor permits access to interior tissues and includes generally longitudinally extending members moveable respecting one another at a position of connection between, having tip portions remote from the connection position and separating from each other upon relative pivotal movement of the members. The retractor further preferably includes means for urging the members pivotally respective one another to separate the tip portions one from another and means for retaining the members at a position at which the tip portions are separated.

10 Claims, 4 Drawing Sheets

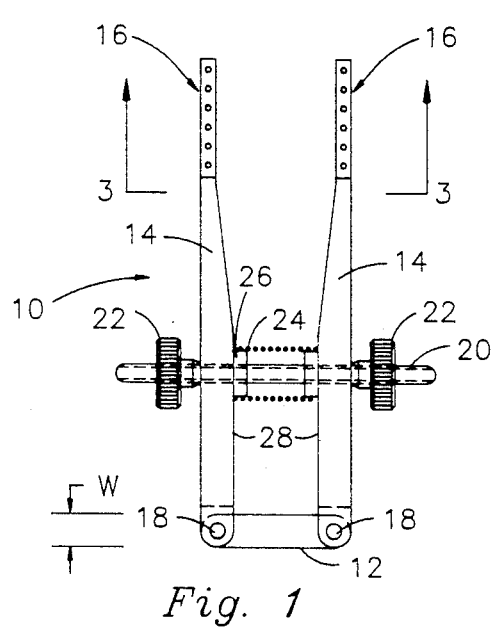
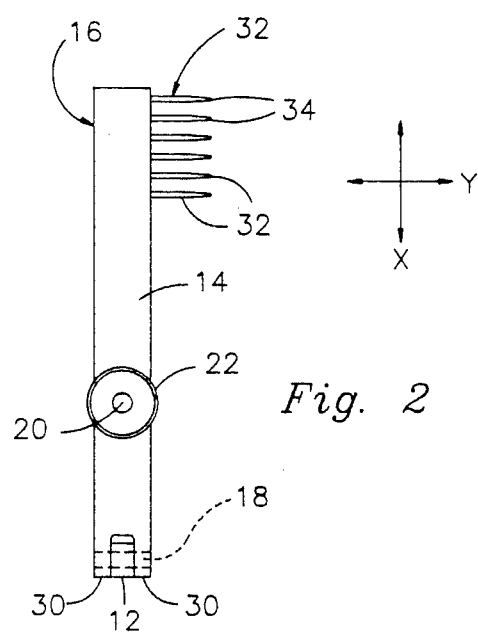
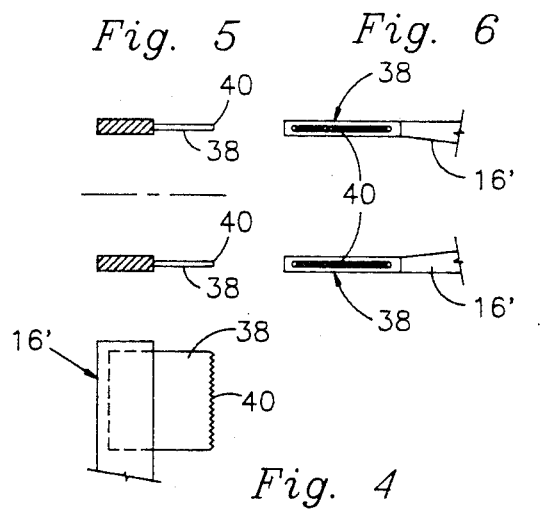
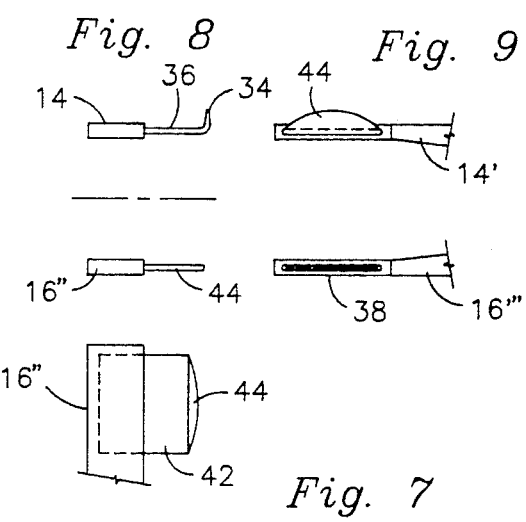

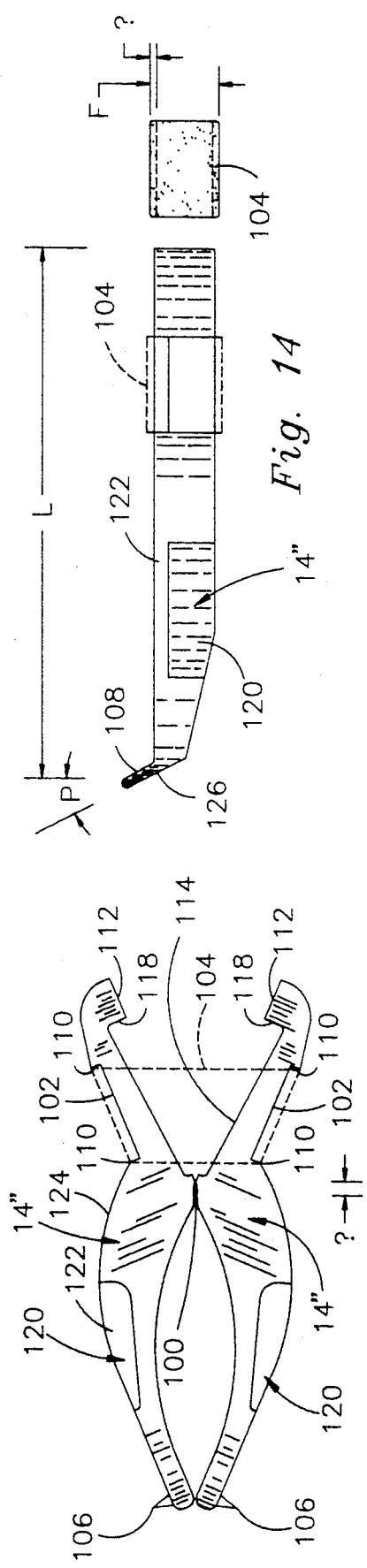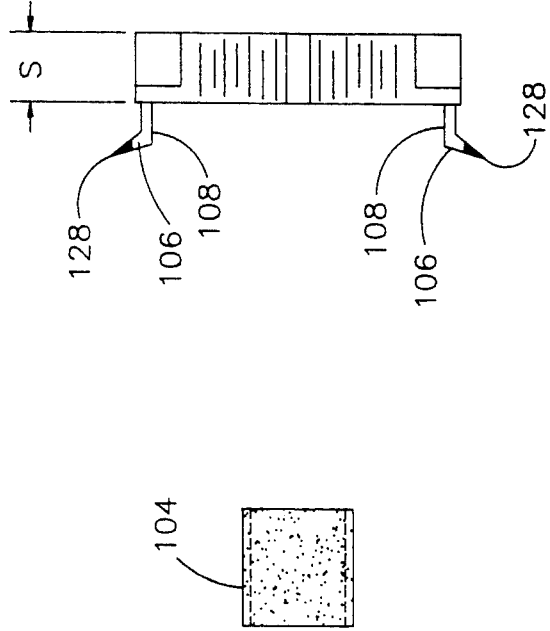

SELF-RETAINING REFRACTOR

FIELD OF THE INVENTION

This invention relates to the field of medicine, specifically to surgery and to tools and instruments used by surgeons during surgical procedures.

BACKGROUND OF THE INVENTION

Small lacerations, requiring wound exploration for repair of tendons, repair of nerves or for removal of foreign bodies, are an extremely common problem confronting surgeons, emergency room physicians and family practitioners dealing with minor traumas. Additionally, medical practitioners are frequently confronted with small skin or subcutaneous lesions. These small surgical or traumatic wounds present a special problem of obtaining adequate exposure of internal tissues and structures so that the surgeon, physician or other medical professional can adequately see the interior tissues and structures in order to access damage, form a plan of treatment and the like.

DESCRIPTION OF THE PRIOR ART

Current surgical practice in providing access to small lacerations requiring wound exploration for tissue repair, diagnosis and the like frequently is to have an assistant to the physician or surgeon hold small skin hook-retractors in place, thereby holding the skin open and exposing the interior tissue. This practice requires an extra pair of hands, namely those of the assistant. This unnecessarily occupies valuable medical assistant personnel and increases the risk of contamination of the wound.

Respecting printed prior art, three (3) United States patents are generally relevant respecting this invention. In descending numerical order these U.S. Pat. Nos. are 4,034,746; 3,916,907 and 2,234,715. Of these patents, '907 and '946 are the most relevant.

The '907 patent discloses a spreader instrument for use in performing spinal fusion, having a spring attached to two (2) gripping arms, where the spring is located on the opposite side of a pivot from plate-equipped tips of the arms; the plate-equipped tips are designed to spread vertebra, to assist in performing spinal fusion surgery. The plate-equipped ends or tips of the arms are configured for retracting vertebra which have been previously drilled to provide a receptacle hole of specific shape.

The '746 patent discloses a retractor having a mechanism for locking the retractor at fixed positions of retraction. The '746 retractor is relatively large.

U.S. Pat. No. 1,264,393 is also known to applicant. However, applicant does not concede that the field of the '393 patent invention, namely automotive repair, is relevant to surgery and emergency room practice or that prior art from the automotive repair field, such as the '393 patent, is properly cited against this application.

The '393 patent shows a spring-like mechanism forming a part of a pliers-type tool, used to bias the tool toward the closed position. Structure at the ends of the arms or tips of the pliers grips piston ring material in order to insert piston rings into desired position.

The '715 patent discloses a retracting instrument used by morticians. The retractor allows the mortician access to arteries or veins while maintaining both hands free to work.

The '300 patent discloses a retractor similar to that disclosed by '715. Ends of the '300 retractor appear to be adapted for engaging animal teeth.

While applicant is aware of the '300 patent, applicant does not concede that the field of veterinary dentistry is an analogous field to that of surgery and emergency room practice such that prior art from the field of veterinary dentistry is properly applicable in evaluating the patentability of this invention.

SUMMARY OF THE INVENTION

As used herein the term "self-retaining" denotes a retractor which, once positioned in place holding open skin at a wound, remains in position, continuing to hold open the skin at the wound without requiring continuous application of manual or tactile force by the attending physician or other health care professional.

In one of its aspects, this invention provides a disposable self-retaining retractor for holding open skin at a wound to permit access to interior tissue for diagnosis and developing a course of treatment. The retractor may include connected generally longitudinally extending finger members adapted for relative movement respecting one another pivotally about the connection. The finger members have tip portions remote from the pivotal connection. The tip portions of respective finger members separate from each other upon relative pivotal movement of their respective finger members. The finger members and their pivotal connection are preferably an integral single piece of injection molded plastic. Means are provided for urging the finger members to pivotally move respecting one another about the pivot point to separate the respective tip portions one from another.

Means may also optionally be provided for retaining the finger members at an adjustably selected position at which the respective tip portions are separated from one another by a distance which by optionally be adjustably preselected. The retaining means preferably operate by opposing force applied by the urging means to the finger members.

The longitudinally extending finger members preferably pivotally move in a reference plane.

The tips of the finger members may be fabricated so that they curve in two planes which are orthogonal to one another and to the reference plane, thereby having a compound curve shape. The tip portions may lie in planes skew to the reference plane. The tip portions of respective finger members are not necessarily in the same plane.

The tip portions may connect to the finger members by intermediate portions which reside generally in a plane skew to the reference plane.

And yet another of its aspects this invention provides a disposable self-retaining retractor, for holding open skin at a wound to permit access to interior tissue, which includes a base and a pair of generally longitudinally extending finger members having respective tip portions separating from one another upon relative movement of the members The members are adapted for relative movement respecting one another about at least one pivotal connection to the base. The finger members have tip portions remote from the pivotal connections. The tip portions of respective fingers separate from each other upon relative pivotal movement of the finger members. The retractor further includes means for urging the finger members to pivotally move respecting one another about the pivot point, to separate respective tip portions one from another. The retractor may yet further include means opposing force applied by the urging means, for retaining the finger members at an adjustably selected position at which the respective tip members are separated from one another by an adjustably preselected distance.

The longitudinally extending finger members pivotally move in a reference plane. The tip portions may have extremity portions defining ends of the respective finger members, where the tip portions are skew to the reference plane. The retractor may further include intermediate portions, connecting finger members to the tip portions, residing in a plane skew to the reference plane and to a plane in which the tip portions reside. The tip portions and/or the intermediate portion may have a compound curve shape.

DESCRIPTION OF THE DRAWINGS

FIG. 1 is a front elevation of a self-retaining retractor manifesting a first embodiment of the invention.

FIG. 2 is a side view of the self-retaining retractor illustrated in FIG. 1.

FIG. 3 is a sectional view taken at arrows 3—3 in FIG. 1.

FIG. 4 is a partially broken side view, taken at the same general position as FIG. 2, showing an alternate embodiment of the tip portion of the self-retaining retractor.

FIG. 5 is a view taken at a position similar to that of FIG. 3, depicting the alternate embodiment of the tip portion of the retractor illustrated in FIG. 4.

FIG. 6 is a side elevation, taken looking from the right side in FIG. 4, of the tip portions of the self-retaining retractor in the alternate embodiment illustrated in FIG. 4.

FIG. 7 is a broken side view, similar to that of FIG. 4, illustrating yet another alternate embodiment for the tip portions of the self-retaining retractor.

FIG. 8 is a view similar to that of FIG. 5, taken at arrows 3—3 in FIG. 1, of still another alternate embodiment of the tip portions of the self-retaining retractor, with one of the tip portions formed according to the embodiment illustrated in FIG. 7.

FIG. 9 is a view similar to that of FIG. 6, depicting still yet another alternate embodiment of the tip portions of the retractor, with one of the tip portions formed according to the embodiment illustrated generally in FIG. 7 and in the lower portion of FIG. 8.

FIG. 13 is a front elevation of the preferred embodiment of the retractor of the invention.

FIG. 14 is the top view of the embodiment of the invention illustrated in FIG. 13.

FIG. 15 is a left-side elevation of the embodiment of the invention illustrated in FIG. 13.

FIG. 16 is a front elevation of the preferred embodiment of the retractor of the invention, taken at position similar to FIG. 13, showing the retractor of the invention positioned with the skin retaining points maximally separated.

Figure 11:
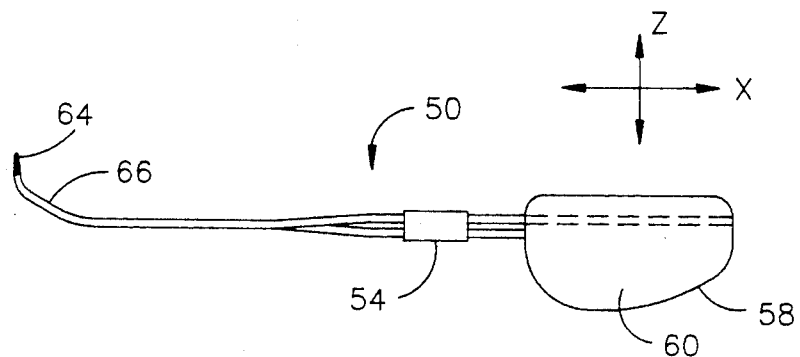
FIG. 11 is a top view of the self-retaining retractor illustrated in FIG. 10.

In the drawings, parts corresponding to those described in the following written description of the preferred embodiments and best mode known for practicing the invention are identified with corresponding numbers. Prime notation is used to denote those parts in the various embodiments depicted in the drawings which correspond one to another.

DESCRIPTION OF THE PREFERRED EMBODIMENTS AND BEST MODE KNOWN FOR PRACTICING THE INVENTION

Referring to the drawings, particularly to FIGS. 1, 2 and 3, a disposable self-retaining retractor for holding open a skin wound to permit access to interior tissue is designated generally 10 and includes a base 12. The retractor further includes a pair of generally longitudinally extending finger members 14 having respective tip portions generally designated 16 separating from one another upon relative movement of finger members 14 respecting one another. Finger members 14 are pivotally connected to base 12 by a pair of pins 18 defining pivotal connections of finger members 14 to base 12.

A rod 20 passes through a passageway formed in finger members 14 and is preferably externally threaded, over at least a portion of the axial length of rod 20, to receive knurled thumb-screw members 22 threadedly engaging rod 20 about the external surface thereof. The external threads on rod 20 have not been illustrated. Similarly, the internal threads within knurled thumb-screw members 22 have not been illustrated.

A coil spring 24 fits around cylindrical fitments 26 formed on mutually facing surfaces 28 of finger members 14. Coil spring 24 urges finger members 13 to pivotally move respecting one another about pivot points defined by pins 18 engaging base 12. As spring 24 urges finger members 14 to so-move, outwardly facing surfaces 30 of finger members 14 contact inboard portions of knurled thumb-screw members 22 and are constrained against further pivotal movement. This results in tip portions 16 being retained at a fixed position respecting one another. That position may be adjusted by rotating knurled thumb-screw members 22 on rod 20 thereby moving thumb-screw members 22 either closer to or farther from one another.

As illustrated in FIG. 2, the ends of finger members 14 in which pins 18 reside are configured generally as a yoke having separated yoke portions 30. Base 12 is configured to fit between yoke portions 30. Base 12 has width, designated by dimension W in FIG. 1, less than distance yokes 30 extend from a central portion of finger members 14. This facilitates pivotal movement of finger members 14 about pins 18 without binding against base 12.

In the embodiment illustrated in FIGS. 1, 2 and 3, tip portions 16 include a plurality of blades 32, each of which has a pointed extremity 34 which is preferably generally perpendicular to a shaft portion 36. The plurality of blades define ends o respective finger members 14.

Each blade 32 preferably includes a shaft portion 36, illustrated in FIG. 3, where shaft portion 36 extends from finger members 14 in a first transverse direction. The first transverse direction is identified by axis Y in FIG. 2; axis X designates the longitudinal direction. Extremities 34 extend from shaft 36 in a second transverse direction respecting longitudinal direction X; this second transverse direction is identified by axis Z in FIG. 3.

In the embodiment illustrated in FIGS. 1, 2 and 3, to facilitate disposability of the self-retaining retractor, base 12 and finger members 14 are preferably plastic. Likewise, rod 20 and knurled thumb-screw members 22 may also be plastic. Blades 34 are preferably metal and are preferably molded in place as finger members 14 are molded. Pins 18 may also be plastic. This substantially all-plastic construction provides a low cost, inexpensive-to-manufacture retractor which, because of its low cost, can be discarded after a single use.

The geometry of blades 32, having extremity portions 34 extending in a direction transverse to both the longitudinal direction of elongation of finger members 14 and the direction of elongation of shaft 36, facilitates hooking extremities 34 under the skin at a wound so that tip portions 16 of retractor 10 spread apart, due to the action of coil spring 24. Extremities 34, having hooked the skin at the wound, separate and hold the skin apart, permitting the physician or other health professional access to the wound interior. A preferred configuration of blades 32, whereby they are formed so that they curve simultaneously in two (2) planes or directions respecting the longitudinal direction, facilitates this skin separating and holding action of the retractor. (This preferred shape of the blade tips is best illustrated in connection with the embodiments illustrated in FIGS. 10, 11 and 12.) For strength, blades 32 are preferably stainless steel.

FIGS. 4, 5 and 6 illustrate an alternate embodiment for the construction of tip portions 16. As illustrated in FIG. 4, the tip portions 16 may, alternatively, be provided with a saw-tooth blade, designated 38 in FIG. 4. Blade 38 is preferably stainless steel and is elongated in the X or longitudinal direction. Blade 38 has teeth 40 formed on the end thereof, where teeth 40 project in the transverse direction indicated by axis Y in FIG. 4. Blade 38 is preferably fixedly molded in place when finger members 14 are molded.

FIG. 7 illustrates yet another embodiment for the tip portions 16 of finger members 14. The embodiment illustrated in FIG. 7 includes a blunt nose blade designated generally 42; the nose portion 44 of blade 42 is gently rounded. This construction may be useful in holding open large or deep wounds where access is required to tissues well inside in the body and more tissue than just the skin must be held open for the physician to access the deep interior portion of the wound. Like blades 32 and 38, blade 42 is preferably stainless steel and is preferably molded in place when finger members 14 are molded.

Rounded nose 44 may be constructed in a variety of geometries according to the particular type of wound with which a given self-retaining retractor will be used. The rounded shape of nose 44 is illustrated in FIG. 7, in the lower portion of FIG. 8 and in the upper portion of FIG. 9.

For certain applications it may be advantageous to have one of the tips of the retractor formed in the hook or blade configuration generally illustrated in FIG. 3, whereby the blade has a shaft portion 36 and a pointed extremity 34, and to have the remaining tip portion of the remaining finger member formed with a rounded nose member 44, as illustrated in FIG. 7. Such an arrangement is depicted in FIG. 8. Similarly, it may be desirable to have one of the tips of the finger member equipped with a serrated or saw-tooth blade 38 and the tip of the remaining longitudinally finger member equipped with a rounded nose 44. Such an arrangement is illustrated in FIG. 9. In other words, the various tip configurations disclosed for use in practicing the invention may be mixed and matched, according to the particular characteristics of wounds with which a particular embodiment of the invention is to be used.

Figure 10:
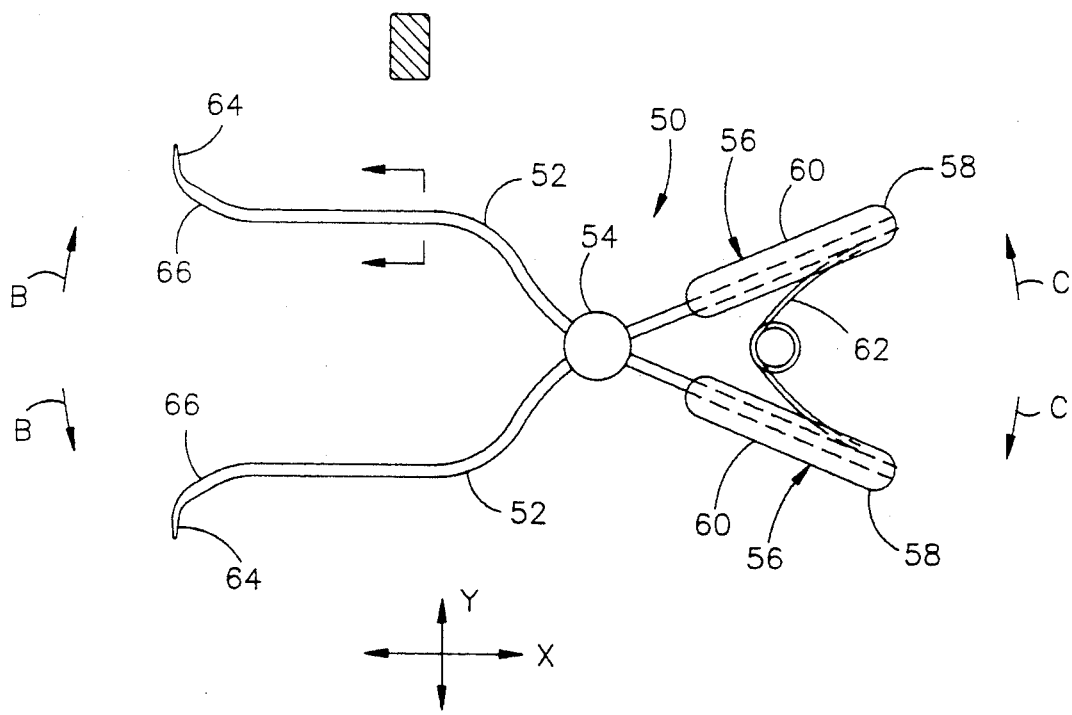
FIG. 10 is a side elevation of yet another embodiment of a self-retaining retractor manifesting aspects of the invention.

FIGS. 10 and 11 illustrate yet another embodiment of a disposable self-retaining retractor for holding open skin at a wound to permit access to interior tissue. In FIG. 10, the retractor is designated generally 50 and includes a pair of pivotally connected generally longitudinally extending finger members 52 adapted for relative movement respecting one another at their pivotal connection 54. Finger members 52 have tip portions 56 remote from pivotal connection 54. Tip portions 56 separate from each other upon relative pivotal movement of finger members 52 at their pivotal connection 54. Finger members 52 are preferably stainless steel and further preferably have plastic handle portions 58 molded in place. Handle members 58 are sized to permit a physician to use the thumb and forefinger to apply force to finger members 52, causing pivotal motion of finger members 52 at pivotal connection 54, spreading tip portions 56 apart. The relatively flat, wide surface portions 60 of handle portions 58 facilitate application of force by the thumb and index finger.

A wire spring 62, similarly to a conventional safety pin, continuously urges the portions of finger members 52, which are within handles 58, apart. This continuous urging action causes tip portions 56 to be continuously urged to rotate so that tip portion extremities 64 are always being urged in a direction indicated by arrows B in FIG. 10. This results from wire spring 62 continuously urging the portions of finger members 52 embedded in handles 58 to move or rotate about pivotal connection 54 in the direction indicated by arrows C in FIG. 10.

Finger members 52 in FIG. 10 may be considered to rotate respecting one another in a reference plane defined by the plane of the paper. The tip portions of finger members 52 at the opposite ends of finger members 52 from tip portions 56 include extremities 64 connected to the main portions of finger members 52 via intermediate portions 66.

Finger members 52 are longitudinally elongated and extend generally in the direction of the X axis illustrated in FIGS. 10 and 11. Intermediate portions 56 of finger members 62 curve as illustrated in FIG. 10 so that extremities 64 extend generally in the Y direction illustrated in FIG. 10. Additionally, tip portions 56 are formed of a ribbon-like portion of stainless steel so that the ribbon-like material may be formed into a curve about or around the longitudinal axis of the ribbon-like material and also formed into a curve along lines which are transverse to such longitudinal axis; the tip points defined by extremities 64 are preferably curved in two planes, effectively in the form of a compound curve. This facilitates hooking and holding tissue at the wound site.

Figure 12:
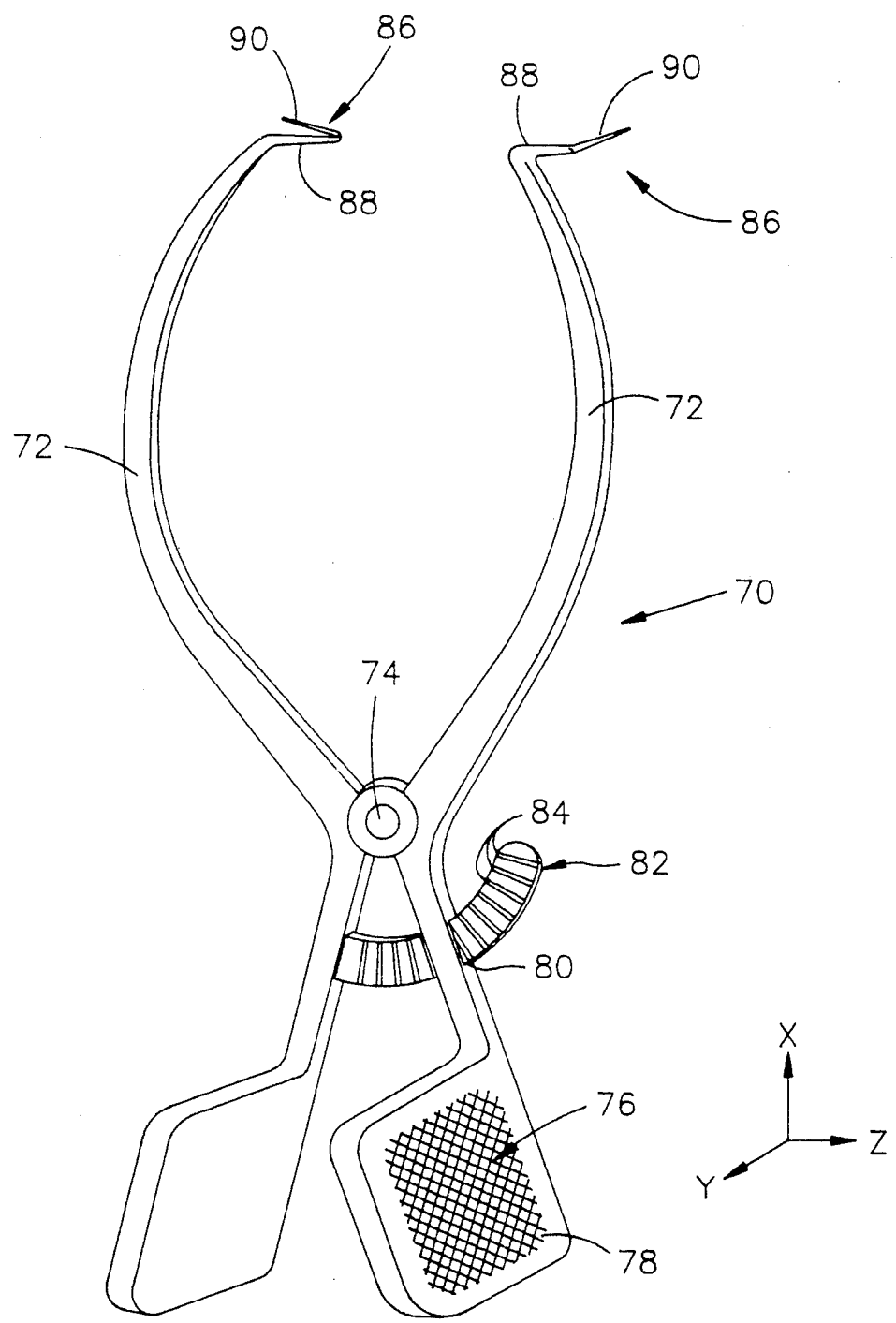
FIG. 12 is an isometric view of a self-retaining retractor manifesting yet another embodiment of the invention.

In FIG. 12 another embodiment of a retractor manifesting aspects of the invention is designated generally 70 and includes longitudinally elongated, pivotally connected arm members 72 joined together at a pivotal connection defined by a rivet or other suitable pivot pin 74. Each arm 72 includes a pad portion 76 formed at one longitudinal extremity of the arm, where pad portion 76 facilitates gripping by the thumb and forefinger of the physician or other health care professional. Pad 76 preferably has serrations 78 to facilitate non-slip contact.

One of arm members 72 includes a slot 80 while the other arm member 72 includes a blade 82 adapted for sliding engagement with slot 80. Blade 82 includes ridges or relief groove 84 adapted for complemental mating with a corresponding groove or ridge formed within slot 80; this groove or ridge is not illustrated in the drawings. The complemental mating of grooves or ridges 84 with their corresponding structure within slot 80 serves to maintain arms 72 at a selected position, thereby providing the self-retaining feature.

The ends of arms 72 remote from pads 76 are formed into hook-like finger members designated generally 86. These finger members include intermediate portions 88 which extend in the direction of axis Y, generally perpendicular to a plane in which the X and Z axes are located and in which arms 72 rotate when they pivotally move respecting one another.

Intermediate portions 88 lead to tip portions 90 which extend away from intermediate portions 88 and arms 72 in a plane skew to the three orthogonal planes in which the respective pairs of axes X and Y, Y and Z and X and Z reside. Additionally, tip portions 90 are curved respecting the X, Y and Z axes and preferably have a ribbon-like configuration which is, in turn, curved respecting lines drawn transversely to an axis of elongation of tip portion 90.

In FIG. 13, the preferred embodiment of the disposable self-retaining skin or micro-retractor of the invention is designated generally 10″ and includes a pair of pivotally connected generally longitudinally extending members 14″ which are moveable respecting one another at a pivotal connection therebetween defined by a hinge portion 100. Means for urging or biasing longitudinally elongated members respecting one another about their connection position towards a position at which the skin holding tip portions of the longitudinally extending members are maximally separated are provided. The urging or biasing means may be in a form of a rubber band or other elastomeric member, or even a spring, which may be slipped into or around and over a recess 102 formed in each of the longitudinally extending members 14″, where the rubber band or other elastomeric member or spring has been identified 104 in FIG. 13. A rubber band is preferred for the means for biasing or urging members 14″ pivotally respecting one another.

Members 14″ are respectively equipped, proximate the extremities thereof which are remote from recesses 102 receiving urging means 104, with a point or skin hook 106, which may be of the general conical shape illustrated in FIGS. 13, 14, 15 and 16 or may even have the curved ribbon-like configuration, with the hooks curving in two planes to provide a compound curve, as described generally respecting the embodiment of the invention illustrated in FIGS. 10 through 12. In the embodiment illustrated in FIGS. 13 through 16, each longitudinally extending member 14″ has been illustrated with only a single point or skin hook 106. Multiple points or skin hooks may be provided at the relevant extremities of members 14″.

Skin hooks 106 connect to longitudinally extending members 14″ via arm members 108 extending generally transversely from fingers or longitudinal members 14″ as illustrated in FIG. 15.

Recesses 102 may be formed in longitudinally extending members 14″ and are preferably bounded by notches 110 formed perpendicular to the bottoms of recesses 102. Notches 110 retain the urging means defined by a rubber band or other elastomeric or resilient member within recesses 102. Where the urging means is a rubber band such as illustrated as 104 in FIG. 14, it is preferable that the rubber band have thickness less than or at the most equal to the depth of recesses 102 as defined by notches 110.

Fingers or longitudinally extending members 14″ further are preferably equipped with abutment surfaces 112 formed to be in facing contact with one another when urging means 104 urges together the two portions of fingers 14″ about which urging means 104 are wrapped. When this occurs, surfaces 112 abut one another thereby preventing further closure of the portions of fingers or longitudinally extending members 14″ which are to the right of hinge member 100 in FIG. 13, towards one another. Hence, when abutting surfaces 112 contact one another, this defines a position of maximum opening or spread between skin hooks 106.

The maximum spread of skin hooks 106 may be controlled according to the dimensions chosen for longitudinally extending members 14″ and the amount by which abutting surfaces 112 extend from inwardly facing surfaces 114 of the portions of fingers or longitudinally extending members 14″. For strength purposes, abutting surfaces 112 preferably connect to inwardly facing surfaces 114 via perpendicular shoulders 118.

The portions of fingers or longitudinally extending members 14″ to the left of hinge member 100 in FIG. 13 are equipped with recesses 120 which are suitably curved and adapted for comfortable receipt of either the finger and thumb pads of the attending physician or other health care professional or the tips of an instrument which may be used to grip and to put into place the retractor. Recesses 120 preferably do not extend entirely across the transverse width of longitudinally extending finger members 14″; this is illustrated in FIG. 14.

There may be ridges or shoulders 122 bordering recesses 120 and which may be formed along the sides of longitudinally elongated finger members 14″ from which arms 108 extend. Ridges or shoulders 122 when contacted by the lateral portions of the attending physician's thumb and index finger, provide the attending physician with a tactile sensation and feedback respecting the location of arms 108 and, most importantly, skin hooks 106. This may be exceedingly important if the physician's vision is occluded, due to the location of the wound in question.

Transversely outwardly facing surfaces of the retractor illustrated in FIGS. 13 through 16 are generally curved; surface 124 is typical. These smoothly curved outer surfaces help to prevent the retractor from entangling loose garments, threads, stitching and the like which may be present in the vicinity of the wound.

The connection positive or hinge means defined by a thin web or ridge or knob of plastic material 110 is preferably transversely elongated, where the transverse direction is perpendicular to the paper respecting FIG. 13, over the entire transverse width of longitudinally elongated finger members 14″. This preferable transverse elongation of hinge means or web 100 provides strength and stability against lateral or transverse shifting of one of longitudinally elongated finger members 14″ vis-a-vis the remaining one of finger members 14″. Prevention of longitudinal shifting is important in order to assure that skin hooks 106 are generally aligned and located in a common plane when those skin hooks move arcuately as the retractor opens and closes.

Arms 108 are preferably perpendicular to longitudinally elongated finger members 14" and preferably extend somewhat transversely from longitudinally extending finger members 14" in a direction which is offset from the axis of hinge means 100.

Prior to use, a rubber band or other urging means 104 is placed around the portions of longitudinally extending finger members 14" extending to the right of the connection point defined by hinge means 100 in FIGS. 13, 14 and 16. The rubber band 104 is retained within recesses 102 by notches 110. In FIGS. 13, 14, 15 and 16 rubber band 104 is shown in dotted lines in the installed position on longitudinally elongated finger members 14". Because urging means 104 is preferably attempting to contract to achieve a relaxed state, urging means 104 continuously urges the portions of finger members 14" which are to the right of hinge or connection point 100 in FIG. 13 towards one another, until abutment surfaces 112 contact At this position skin hooks 106 are separated by a maximum distance.

When the attending physician or other health professional utilizes the disposable retractor, the physician may grasp the disposable micro-retractor by placing his or her thumb and index finger into respective recesses 120 and applying tactile force to recesses 120. (Alternatively, the physician may use an instrument to manipulate, install and/or remove the retractor.) Force manually applied by the physician or other health professional tends to urge skin hooks 106 towards one another, with the portions of longitudinally extending finger members 14" to the left of hinge 100 in FIG. 13 moving towards one another.

As a result, the portions of longitudinally extending finger members 14" to the right of connection point or hinge 100 rotate about the connection point or hinge 100 and move away from one another, against the biasing force provided by urging means 104. In this manner, the physician or other attending health care professional reduces the distance by which skin hooks 106 are separated and may insert skin hooks 106 underneath the skin, on respective sides of a wound of interest.

By then reducing the tactile force applied to recesses 120, until the force applied is overcome by force applied by urging means 104, the portions of longitudinally extending fingers 14" to the right of hinge member 100 rotate towards one another and, concomitantly, the portions of longitudinally extending finger members 14" to the left of hinge means 100 in FIG. 14 rotate about hinge means 100 away from one another until abutting surfaces 112 contact. At this position skin hooks 106 are spaced apart from one another a maximum distance. As a result, the skin retained by hooks 106 is spread apart, allowing the physician or other attending health professional access to the wound.

The disposable retractor illustrated in FIGS. 13 through 1 is, with the exception of urging means 104, preferably injection or compression molded in the form a single piece of thermoplastic. Hinge means 100 is an integral portion of the plastic structure of the retractor and is formed as the plastic portion of the retractor is molded. Depending of the particular characteristics and resistance to movement one wishes to achieve, hinge means 100 may be a relatively thick portion of thermoplastic, having significant elevation and width when considered respecting FIG. 13. Alternatively, if very little resistance to movement and great freedom of motion is desired for longitudinally extending finger members 14" vis-a-vis one another, hinge means 100 may be a mere sliver or tiny web of thermoplastic.

While it is preferred that the micro-retractor (other than urging means 104) illustrated in FIGS. 13 through 16 be molded in a single injection molding operation to provide a single, integrally formed micro-retractor, it is also within the purview of the invention to provide skin hooks 106 as metal hook-like members which are secured in place during the molding process, much as described above with respect to the embodiments of the invention illustrated in FIGS. 1 through 8. In such case, where the skin hooks are metal, it is much easier to achieve the configurations described above whereby the skin hooks curve simultaneously in two planes and are in the form of compound curves.

Respecting the embodiment of the micro-retractor illustrated in FIGS. 13 through 16, arms 108 serve to transversely or laterally displace skin hooks 106 from position in the plane in which longitudinally extending finger members 14" rotate about hinge means 100 respecting one another. This lateral or transverse displacement of skin hooks 106 provided by arms 108 permits the physician or other attending health care professional to open exceedingly small wounds, with the retractor being large enough for the physician to comfortably grip between the thumb and index finger or to manipulate and maneuver using an instrument. This is important; if the micro-retractor is excessively small, it becomes difficult to grip and to manipulate so that it loses it effective utility and may cause the physician to inadvertently injure the patient.

In the preferred embodiment of the invention illustrated in FIGS. 13 through 16, longitudinally extending finger members 14" have width or thickness indicated by dimension F in FIG. 14 of preferably about 0.187 inches. Shoulder 122 has thickness illustrated as dimension G in FIG. 14 of preferably about 0.045 inches. Overall longitudinal length of the micro-retractor is preferably about one and one-half inches as indicated by dimension L in FIG. 14. Hinge means 100 preferably has longitudinal thickness and height of about between eight one thousands (0.008) and about fifty one thousandths (0.050) of an inch. Of course, the thickness in the longitudinal direction and the height of hinge means 100 will depend on the properties of the thermoplastic material from which the disposable micro-retractor illustrated in FIGS. 13 through 15 is molded and the degree of stiffness desired when opening and closing of the retractor. Polyethylene, polypropylene and various other polymers such as polyvinylidene fluoride are all believe suitable for practice of the invention; the preferred material with which the dimensions noted above provide good results is the thermoplastic sold by DuPont under the trademark Lexan.

While arm 108 extends generally transversely from longitudinally elongated finger members 14" as viewed in FIG. 15, arms 108 are effectively slightly canted, with respect to the longitudinal direction, from longitudinally extending finger members 14" as illustrated in FIG. 14. In the preferred embodiment of the invention, arms 108 are at about a twenty-five degree (25°) angle from the transverse direction; this angle is denoted P in FIG. 14. The tips of longitudinally extending fingers 14" are preferably tapered as provided by taper surface 126 in FIG. 14; this taper provides a smaller structure at the left hand ends of longitudinally extending finger members 14" when viewed in FIGS. 13 and 14. This facilitates the physician's inspection of the wound while using the retractor.

In FIG. 15, a configuration of skin hooks 106 is illustrated whereby skin hooks 106 extend not only vertically away from arms 108 but may also have tip extremity portions 128 which may extend transversely from the remaining, main portion of skin hooks 106; this facilitates hooking the skin at the open wound.

In the preferred embodiment illustrated in FIGS. 13 through 16, overall width of the micro-retractor, including the ends of skin hooks 106, is about one quarter inch, denoted by dimension S in FIG. 15.

The foregoing describes the preferred embodiment of the invention and the best mode of practicing the invention as currently contemplated by the inventor. However, the invention is not limited to those embodiments and modes illustrated, described and disclosed above; the invention encompasses variations and alterations to the embodiments set forth herein and is defined by the following claims that are intended to cover the invention. Structures which perform substantially the same function in substantially the same way to achieve substantially the same result as the claimed structure are within the purview of the invention.

I claim the following:

1. A retractor for holding open skin, comprising:
   a. a unitary piece including movably connected members having points proximate longitudinal extremities of said members separating from each other upon relative movement of said members and means for retaining said members at a position of maximum point separation when said members are urged towards said position of maximum point separation; and
   b. resilient elastomeric means for urging said members to move about a position of moveable connection therebetween towards said position of maximum point separation.

2. The retractor of claim 1 wherein said resilient elastomeric means is an endless loop.

3. The retractor of claim 2 wherein said loop is a rubber band having width contacting said rotatably connected member greater than rubber band thickness.

4. The retractor of claim 1 wherein said resilient elastomeric means exerts compressive force on said unitary piece.

5. The retractor of claim 1 wherein said unitary piece is homogeneous plastic.

6. The retractor of claim 1 wherein said connected members are connected by hinge means defined by a plastic web.

7. The retractor of claim 1 wherein said members are rotatable relative to one another within a reference plane and wherein said points are of ribbon-like configuration displaced from said reference plane and curved in at least one plane skew to said reference plane.

8. The retractor of claim 1 wherein said points move in a plane parallel to said reference plane upon relative rotation of said members respecting one another.

9. The retractor of claim 1 wherein said resilient elastomeric means lies in said reference plane and is of sinuous configuration.

10. A disposable self-retaining skin retractor permitting access to interior tissue, comprising:
    a. longitudinally elongated members moveable respecting one another about a position of connection therebetween, having tip portions remote from said connection position separating from each other upon relative rotary movement of said members; and
    b. means for biasing members respecting one another about said connection position towards a position at which said tip portions are maximally separated; wherein said connection position is a web and said longitudinally elongated members and said web are an integral single piece of plastic.

* * * * *

UNITED STATES PATENT AND TRADEMARK OFFICE
CERTIFICATE OF CORRECTION

PATENT NO. : 5,176,129

DATED : January 5, 1993

INVENTOR(S) : STEPHEN H. SMITH

It is certified that error appears in the above-identified patent and that said Letters Patent is hereby corrected as shown below:

On the title page, item [54] and column 1, line 2, replace "REFRACTOR" with --RETRACTOR--.

Signed and Sealed this

Fourth Day of January, 1994

Attest:

BRUCE LEHMAN

*Attesting Officer*     Commissioner of Patents and Trademarks